United States Patent [19]

Abts

[11] 4,455,873
[45] Jun. 26, 1984

[54] ULTRASONIC PROBE

[75] Inventor: Leigh R. Abts, Barrington, R.I.

[73] Assignee: Micro Pure Systems, Inc., Smithfield, R.I.

[21] Appl. No.: 327,455

[22] Filed: Dec. 4, 1981

[51] Int. Cl.³ .............................................. G01N 29/00
[52] U.S. Cl. ................................. 73/629; 73/632
[58] Field of Search ........... 73/632, 642, 861.25, 73/861.28, 53, 61.1 R, 61 R, 629, 645

[56] References Cited

U.S. PATENT DOCUMENTS

| | | | |
|---|---|---|---|
| 3,040,562 | 6/1962 | Fitzgerald et al. | 73/645 X |
| 3,239,801 | 3/1966 | McGaughey | 73/642 X |
| 3,269,173 | 8/1966 | Ardenne | 73/642 X |
| 3,310,977 | 3/1967 | McGaughey | 73/642 X |
| 3,816,773 | 6/1974 | Baldwin et al. | |
| 3,898,840 | 8/1975 | McElroy | |
| 3,934,460 | 1/1976 | Sherwin et al. | 73/642 |
| 4,297,886 | 11/1981 | Anikeev et al. | 73/642 |

*Primary Examiner*—James J. Gill

[57] ABSTRACT

A probe for obtaining information about a fluid comprising an electrically-shielded transducer having a lens for focusing energy waves, the transducer being attached to a cable and mounted in a protective sheath supported by a rod, whereby the transducer can be immersed in the fluid and moved around therein to take readings at various locations.

5 Claims, 3 Drawing Figures

ULTRASONIC PROBE

FIELD OF THE INVENTION

This invention relates to obtaining information about a fluid.

BACKGROUND OF THE INVENTION

The background of this invention pertaining to detecting discontinuities in a flowing fluid stream in a narrow conduit is fully set out in my U.S. Pat. Nos. 4,112,773 and 4,214,484, both hereby incorporated by reference.

In addition to obtaining information about fluids flowing in conduits, however, it is also desirable to be able to obtain such information about large volumes of fluids standing in or slowly circulating through large containers.

SUMMARY OF THE INVENTION

I have discovered that an ultrasonic transmitter-receiver having a lens can be sealed in a protective sheath and connected to a cable thereby forming a submersible probe, which probe can be immersed in a fluid and moved around therein to take measurements at various locations.

In a preferred embodiment, an ultrasonic transmitter-receiver having a concave lens and surrounded by an electrically-grounded shield is connected to the end of a cable. The transmitter-receiver is sealed inside a protective sheath, and the cable is encased in a hollow rod so that the transmitter-receiver can be immersed in a fluid and directed to the desired locations for measurements.

In another preferred embodiment, a short conduit having an ultrasonic transmitter-receiver arranged to direct a beam transversely to flow through the conduit is connected to a pump. The conduit and pump are mounted on a rod carrying a cable to the transmitter-receiver. The probe can be placed inside a tank, and when the pump is activated, the fluid will flow through the conduit, and measurements of different portions of the fluid can be taken without moving the probe.

PREFERRED EMBODIMENTS

We turn now to the structure and operation of a preferred embodiment, after first briefly describing the drawings.

DRAWINGS

STRUCTURE

Figure 1:
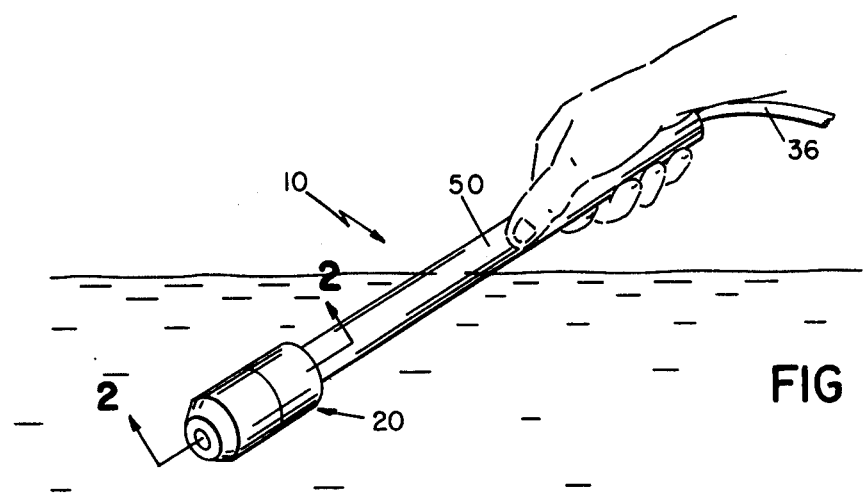
FIG. 1 is a perspective view of the probe of this invention.

Referring to FIG. 1, there is shown a probe 10 having a protective sheath 20 mounted on a hollow rod 50.

Figure 2:
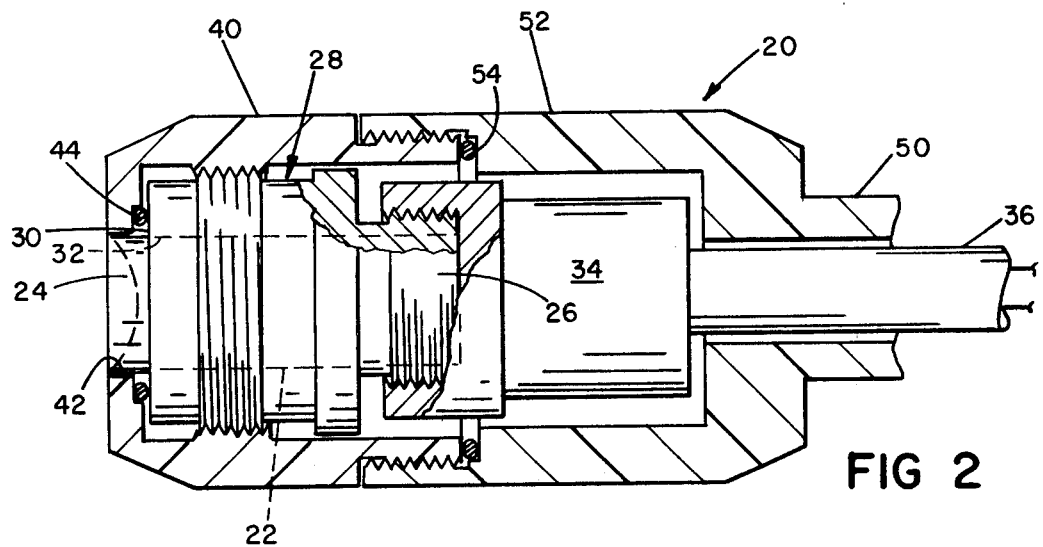
FIG. 2 is an enlarged cross-sectional view of the protective sheath of the probe of FIG. 1.

As shown in FIG. 2, the sheath 20 contains an ultrasonic transmitter-receiver 22 having a concave lens 24 at one end and a twinax Amphanol connector 26 on the opposite end. Transmitter-receiver 22 is the same as that disclosed in my U.S. patent application Ser. No. 187,615, filed Sept. 15, 1980, now Pat. No. 4,365,515, incorporated herein by reference.

Transmitter-receiver 22 is mounted in a central cavity of a casing 28 and held in place by screws (not shown). Casing 28, the outside of which is screw-threaded, has a flat front face 30 with a lens opening 32 through which transmitter-receiver lens 24 extends. The connector 26 of the transmitter-receiver 22 extends from the other end of the casing 28.

Shielded cable connector 34 is attached to the sheath end of a twinax cable 36. Connector 34 is a standard connector, and it mates with the connector 26 of the transmitter-receiver 22.

Sheath cap 40 fits over casing 28. Cap 40 is generally cylindrical and has a small lens opening 42 in one end. The cap 40 is internally screw-threaded. Casing 28 fits in and is secured inside cap 40, and lens 24 is directed out lens opening 42. Casing 28 is sealed to cap 40 by O-ring seal 44.

The rod 50 covers a portion of the cable 36, and the rod 50 has a cylindrical body 52 attached to its lower end. The body 52 connects to the cap 40, and O-ring seal 54 seals the parts together.

The sheath 20 and the rod 50 are made of Teflon ®, although the material may change depending upon the type of fluid in which the probe will be used.

The electronic devices to which the cable 36 is attached are the same as those in my U.S. patent application Ser. No. 136,169, filed Mar. 31, 1980, now abandoned, also incorporated herein by reference.

OPERATION

In operation, protective sheath 20 is assembled thereby sealing the transmitter-receiver 22 from the fluid. The transmitter-receiver 22 is operated in the same manner as in my U.S. patent application Ser. No. 136,169, filed Mar. 31, 1980. The operator, however, may hold the rod 50 at the end opposite the sheath 20 and direct a focused ultrasonic beam from the transmitter-receiver 22 into any place in a container of liquid. Therefore, in a large container in which the particulates to be measured may have settled into the corners or to the bottom, the probe 10 can be directed thereto in order to detect them.

OTHER EMBODIMENTS

Figure 3:
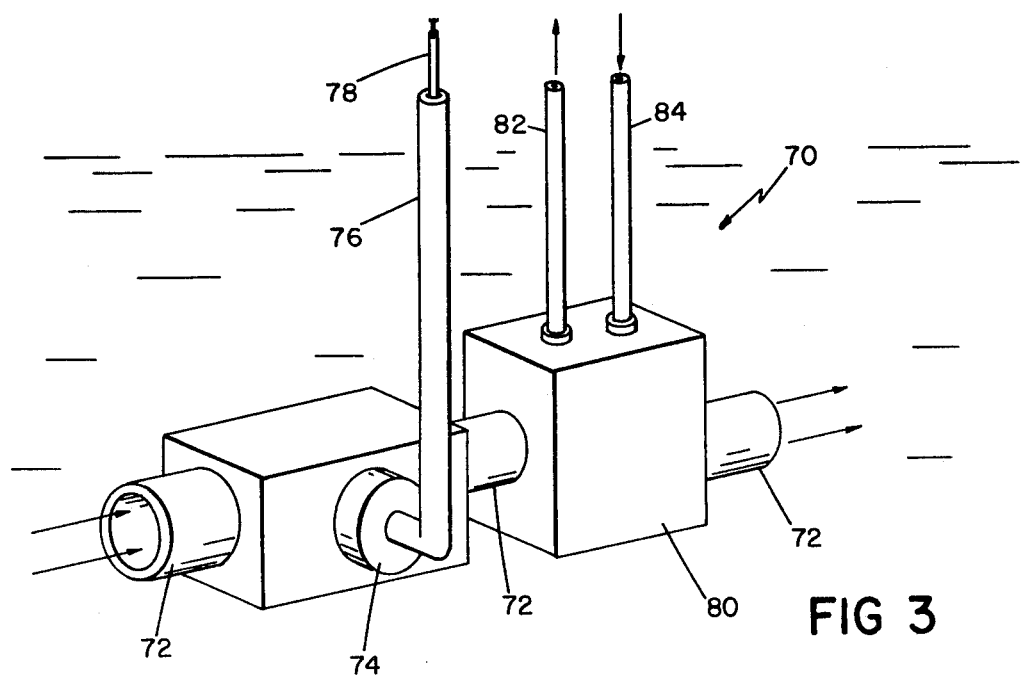
FIG. 3 is a perspective view of another probe of this invention.

Referring to FIG. 3, another probe is shown at 70. Probe 70 comprises a conduit 72, a transmitter-receiver 74 of the same type as that of the preferred embodiment, and a pump 80.

The conduit 72 extends about 8 inches in length, and transmitter-receiver 74 is positioned in the side of the conduit 72 near its intake end so as to direct an ultrasonic beam across the flow therethrough. Rod 76 covers a cable 78 from the transmitter-receiver 74.

Pump 80, which is a small diaphragm type, is positioned near the other end of the conduit 72. Air exhaust and air supply pipes 82, 84 are connected to the pump 80.

In operation, the probe 70 is placed in the bottom of a tank, and the pump 80 is activated. Pump 80 continuously forces fluid through the conduit, and transmitter-receiver 74 detects any discontinuities in this flow. Thus, with the pump in operation, the probe 70 can remain in place, while fluid throughout the container will be circulated past the transmitter-receiver 74.

Other embodiments of the invention will occur to those skilled in the art.

What is claimed is:

1. A hand-held probe for obtaining information about the kind and number of small particulates in a large volume of fluid standing or slowly circulating in a container comprising:
- an ultrasonic transmitter-receiver having a solid concave lens,
    - said transmitter-receiver being disposed in a protective sheath to shield the transmitter-receiver from the fluid,
        - said sheath being positioned on the end of a rod whereby said probe can be directed by hand to various locations in the fluid including the corners of the container so that said transmitter-receiver can direct its ultrasonic energy through said concave lens and into the adjacent fluid and thereby detect the presence of the small particulates by detecting the energy reflected from them.

2. The probe of claim 1 wherein said protective sheath comprises a casing for holding said transmitter-receiver.

3. The probe of claim 1 wherein said rod carries a cable, said cable being attached to said transmitter-receiver.

4. The probe of claim 1 wherein said lens directs ultrasonic energy beams through a lens opening in the end of said sheath.

5. A probe for obtaining information about a fluid comprising:
- an ultrasonic transmitter-receiver having a lens,
    - said transmitter-receiver being disposed in a protective sheath,
        - said sheath being positioned on the end of a rod whereby said probe can be directed to various locations in the fluid,
- said probe further comprising a pump mounted on said rod, said pump having an associated conduit through which said pump forces the fluid and across which said conduit said ultrasonic transmitter-receiver is directed.

* * * * *